United States Patent [19]

Evans et al.

[11] Patent Number: 4,600,015
[45] Date of Patent: Jul. 15, 1986

[54] PATIENT MONITORING APPARATUS AND METHOD

[75] Inventors: John M. Evans, Abingdon, England; Colin C. Wise, Cardiff, Wales

[73] Assignee: Antec Systems Limited, Oxford, England

[21] Appl. No.: 687,742

[22] Filed: Dec. 28, 1984

Related U.S. Application Data

[63] Continuation-in-part of Ser. No. 314,413, Oct. 23, 1981, Pat. No. 4,502,490.

[30] Foreign Application Priority Data

| Oct. 28, 1980 [GB] | United Kingdom | 8034669 |
| Dec. 11, 1980 [GB] | United Kingdom | 8039741 |
| Jun. 26, 1984 [GB] | United Kingdom | 8416219 |

[51] Int. Cl.[4] ............................................. A61B 5/10
[52] U.S. Cl. ..................................... 128/780; 604/97; 604/100
[58] Field of Search ............... 128/774, 780; 604/96, 604/97, 99, 100, 101, 111

[56] References Cited

U.S. PATENT DOCUMENTS

| 3,426,758 | 2/1969 | Harautuneian | 604/100 |
| 4,351,341 | 9/1982 | Goldberg et al. | 604/97 |
| 4,502,490 | 3/1985 | Evans et al. | 128/780 |

Primary Examiner—William E. Kamm
Attorney, Agent, or Firm—Cushman, Darby & Cushman

[57] ABSTRACT

An apparatus for monitoring patient functions, particularly depth of anesthesia includes an oesophageal probe having a balloon located in the patient's oesophagus to provoke contractions thereof; a gas cylinder or pump for applying air or saline solution to the balloon and a sensor for detecting signals indicative of oesophageal contraction, from which signals the depth of anesthesia may be estimated.

16 Claims, 25 Drawing Figures

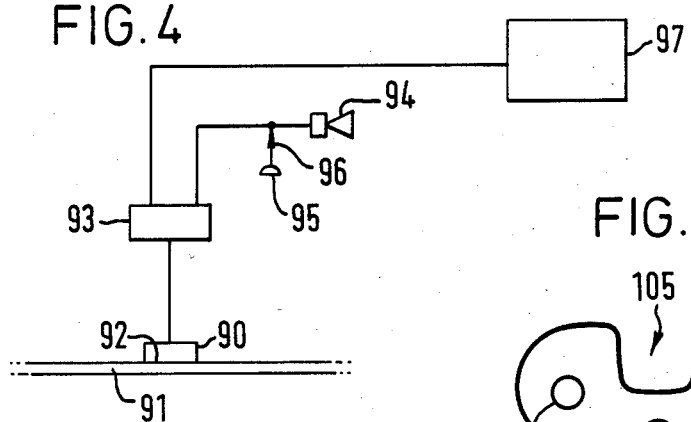
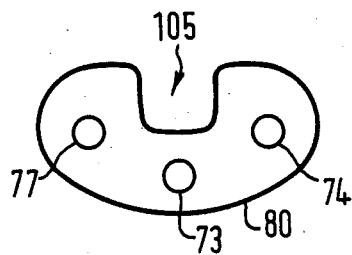
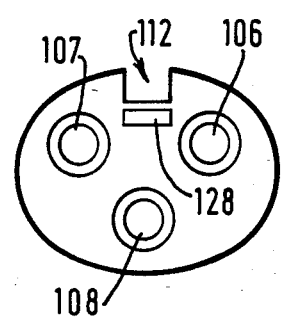
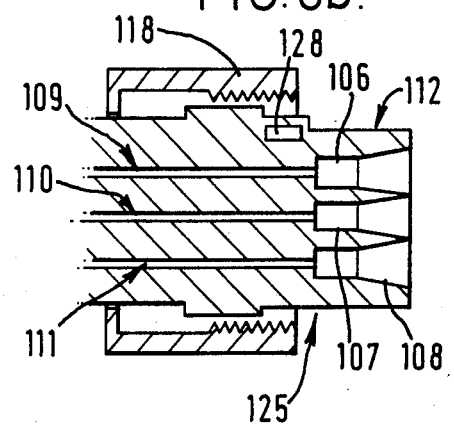
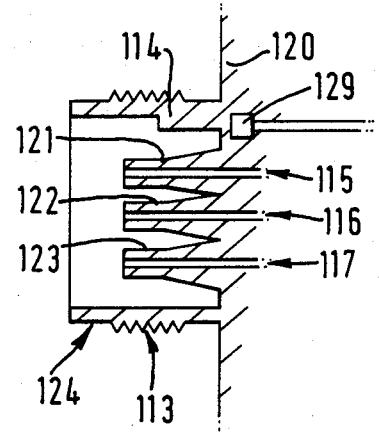

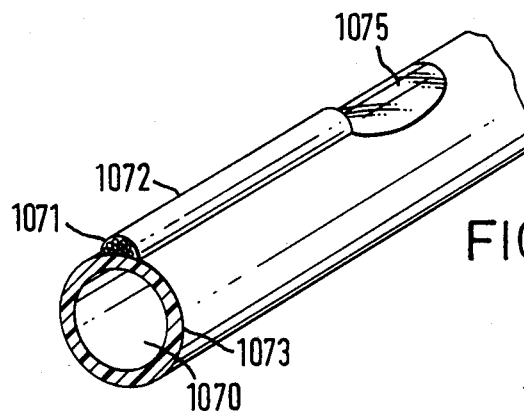
FIG. 11a
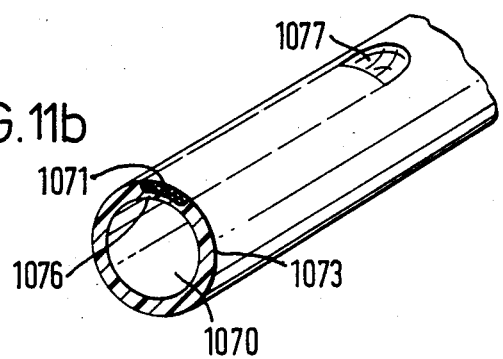
FIG. 11b
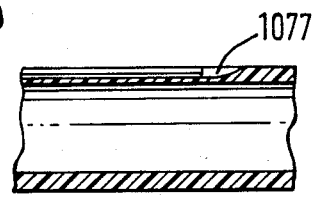
FIG. 12
FIG. 11c
FIG. 11e
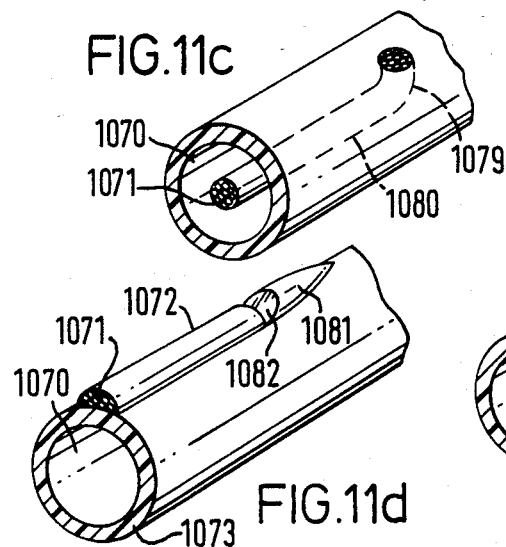
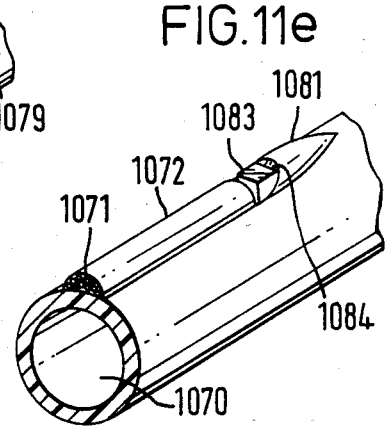
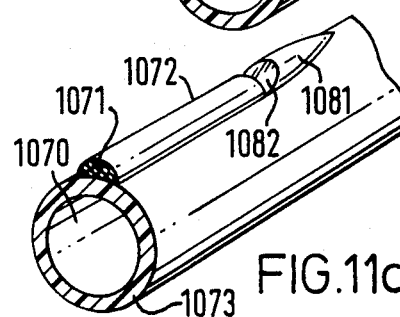
FIG. 11d

PATIENT MONITORING APPARATUS AND METHOD

This application is a continuation-in-part of U.S. patent application Ser. No. 314,413 (now U.S. Pat. No. 4,502,490), filed Oct. 23, 1981 the contents of which are incorporated herein by reference.

This invention relates to apparatus for monitoring various functions of patients, and in particular to apparatus for monitoring the depth of anaesthesia or patients of the kind disclosed in U.S. patent application Ser. No. 314,413. Also included within the scope of the invention are certain novel probes and connectors suitable for use with such apparatus.

As disclosed in the said U.S. application, depth of anaesthesia can be estimated by measuring the amplitude and/or frequency of contractions of the oesophagus of a patient, either with or without stimulation of the oesophagus to provoke such contractions.

We have now discovered that it is of great value to provide either as a part of the apparatus or the probe used with such apparatus means for protecting the oesophagus of the patient from over inflation of the balloon, or leakage of the fluid from the probe.

Accordingly, in a first aspect of the invention, there is provided patient monitoring apparatus comprising an oesophageal probe including an oesophageal balloon for provoking the oesophagus of a patient to cause contractions therein, means, for example a gas cylinder or pump for applying a fluid such as air or saline solution under pressure to the oesophageal balloon, a sensor for detecting signals indicative of oesophageal contractions in the oesophagus of the patient, for example a pressure transducer connected to a lumen in turn connected to a second oesophageal balloon, means for deriving from the said signals an output indicative of the depth of anaesthesia of the patient, for example for driving a chart recorder or controlling the administration of a drug, and means on the probe for protecting the oesophagus of the patient from overinflation of the balloon or leakage of the fluid from the probe.

The means for protecting the oesophagus of the patient from overinflation of the balloon, or leakage of the fluid from the probe, may take the form of an enclosure surrounding at least the provoking balloon, and possibly any other balloons present, for example sensing balloons. Alternatively, the means for protecting the oesophagus may take the form of a lumen open at an end adapted to terminate in use in the oesophagus of the patient, for relieving oesophageal pressure. A third possibility is that the means for protecting the oesophagus may take the form of means on the probe for detecting pressure in the oesophageal lumen, connected to means for generating an alarm signal or for inhibiting provocation of the oesophagus, on rise in pressure in the oesphagus.

Where a protective enclosure is utilised, a pressure or flow transducer or sensor may be used in communication with the internal space of the enclosure, for example either within the enclosure itself, or within a lumen connected to the internal space of the enclosure, and the apparatus may include means for preventing the application of pressure to fluid in the balloon, in response to the pressure or flow sensed by the said transducer.

Where an open-ended lumen is utilised, means may be provided for detecting flow of fluid in the lumen, for example a flow-sensitive transducer may be provided, and may be used to generate an alarm signal. An example of a suitable transducer is a heated thermistor.

The open-ended lumen provides egress from the oesophagus for gas or liquid from the provoking balloon in the event of rupture so that overdistension of the oesophagus does not occur.

Overinflation of the provoking balloon may be detected and avoided by using a closed system with a fixed volume of gas or liquid attached to the lumen leading to the provoking balloon. Conveniently this may take the form of a reservoir of gas or liquid which is connected to the provoking balloon, preferably a syringe, and a system of emptying the reservoir into the provoking balloon. The reservoir may be pressurised, for example it may take the form of a syringe with a plunger, activated by a spring compressed by a mechanical drive, such as a stepper motor. Alternatively, a stepper motor may be used directly to provide compression within the reservoir, typically a syringe. In addition, means may be provided for releasing pressure in the reservoir after each provocation, for example by venting the reservoir, by returning the plunger of the syringe by means of a spring, or preferably using a stepper motor, and means may also be provided for detecting a change in volume or pressure in the provoking reservoir. Such a change would indicate leakage, and provide a signal indicative of such leakage.

Accordingly, in a second aspect of the invention, there is provided patient monitoring apparatus comprising an oesophageal probe including an oesophageal balloon for provoking the oesophagus of a patient to cause contractions therein, means for applying a fluid under pressure to the oesophageal balloon, and means for detecting the pressure rise in the oesophageal balloon resulting from operation of the pressure sensing means.

The detection means is preferably adapted to provide an indication of pressure change in the oesophageal balloon over a predetermined period of time, so as to provide an indication of leakage of fluid from the provoking balloon. The means for applying a fluid under pressure preferably includes means for rapidly releasing pressure from a pressurised vessel into the oesophageal balloon to provide rapid inflation, and for automatically relieving pressure applied to the oesophageal balloon a predetermined period thereafter.

In a particular embodiment means may be provided for deactivating an otherwise active alarm circuit periodically, when part of the pressure generating means, for example a diaphragm or syringe returns to its resting position. Such means may include a reed relay and an alarm circuit with a delay of a few seconds which is periodically inactivated by the reed relay. Thus the reed relay inhibits the alarm circuit, provided that the diaphragm or syringe returns to a position within predetermined limits of its previous resting position. The arrangement is thus such that if fluid is either lost from or gained by the reservoir, the alarm circuit is not inhibited.

Alternatively, as indicated above, the pressure may be measured in the oesophageal balloon. A leak from the closed oesophageal balloon will manifest itself by a negative pressure between provoking impulses, a less than normal pressure during provocation, or a pressure change in the oesophageal balloon over a predetermined period of time after provocation. Therefore by providing a transducer either within the oesophageal provoking balloon itself, or within the lumen attached to it, it is possible to generate an indication of leakage of fluid from the pressure balloon. Signals may be obtained indicative of the pressure within the provoking balloon, and by means of for example a comparator, a signal may be generated if there is a negative pressure between the provoking impulses, a less than normal pressure during the provoking impulse, or a fall in the plateau pressure generated within the provoking balloon. The signal may be used to generate an alarm condition.

However, patients under anaesthesia are frequently given nitrous oxide, and even if there is no leak, nitrous oxide may diffuse through plastic materials into gas spaces within body cavities, and hence increase the pressure of gas within such cavities. It is therefore convenient to provide a vent in the part of the apparatus which is connected to the provoking balloon. A particularly convenient method of achieving this, when the oesophageal provoking balloon is activated by means of a syringe, is to provide a lateral orifice in the syringe. When the syringe is returned to the resting position, the plunger is withdrawn past the lateral orifice, and any excess gas may be vented. During provocation, the plunger of the syringe passes the orifice, and in doing so closes the orifice. A flow sensor, typically a heated thermistor, may be placed adjacent to the orifice in such a way that flow into and out of the reservoir may be monitored. Should a leak occur into or out of the system, the signal from the flow sensor will increase. This can be used to generate an alarm.

In an alternative system of measuring leaks from the provoking balloon, a sensing balloon is utilised to measure contractions in the oesophagus, as descried in U.S. patent application Ser. No. 314,413, and means are provided associated with the pressure sensing and measuring balloon for measuring long term changes in average pressure. Thus, the signal from a monitoring transducer may be fed to a comparator, and if the output measured corresponds to a pressure of more than a preset threshold, for example 50 mm Hg for more than a predetermined time, for example 10 seonds, an alarm may be activated.

Means may be provided for inhibiting the provocation of the oesophagus, if any alarm condition as indicated above exits, until the device is reset by a clinician.

In accordance with yet a further aspect of the invention, it has been determined that useful further information can be obtained regarding the condition and in particular degree of oxygenation of a patient by viewing the internal surface of the oesophagus of the anaesthetised patient. If the oxygen level in blood falls, the blood becomes increasingly blue instead of red. By comparing the proportion of red and infra-red light absorbed by blood the level of oxygenation may be determined. This level may be measured by comparing the reflectance of light at convenient wavelengths in the red and infra-red spectrum when the oesophagus is illuminated either by white light or monochromatic light of those wavelengths. The surface of the oesophagus may be used to reflect light and the oxygenation of the blood in the vessels close to the surface may thus be measured. Light may be conducted to the surface of the oesophagus by a fibroptic channel, and the reflected light collected by a second fibroptic channel. Alternatively and preferably, the light may be conducted to, or collected from the wall of the oesophageal probe by applying the generators or sensors or fibroptic channels leading to the generators or sensors to some part of the probe, conveniently the wall of the external end of the probe, thus using the wall of the probe as one of the light channels.

The fibre optic channel or channels may conveniently be provided as a part of a probe as described in European patent application No. 0050983, or as described hereinafter.

The pressure within the oesophagus may fluctuate from causes other than oesophageal muscle activity. These pressure fluctuations are smaller in amplitude than those seen during oesophageal muscle activity, those due to respiration, either spontaneous or artificial, being typically of the order of 10 mm Hg, and those due to cardiac activity being typically of the order of 1 mm Hg. However, these fluctuations may also be monitored to give additional information to the physician about respiratory and cardiac function.

The pressure within the oesophagus fluctuates with cardiac activity. This fluctuation will increase with increased cardiac activity, and vice versa. The changes are small.

The oesophageal pressure will vary with changes in the intrathoracic pressure. The intrathoracic pressure will be reduced by the activity of the diaphragm in spontaneous respiratory activity in a cyclical fashion, thus producing parallel falls in oesophageal pressure. These fluctuations will be produced by spontaneous respiratory effort during spontaneous respiration or during controlled ventilation or intermittent mandatory ventilation, and the size of the fluctuation will increase with increasing respiratory effort. Such increased respiratory effort may be seen with sighing, a reduced respiratory depression produced by therapeutic intervention (as for example in the treatment of myaesthesemia, drug depression) or a reduction in the degree of depression of respiratory effort as seen in the reversal of relaxant drugs or a decrease in level of anaesthesia in spontaneously breathing anaesthetised patients. The fluctuations will also increase with obstruction of the airway, an increase in the airway resistance, or in certain modes of failure of breathing circuits.

The fluctuations may be reduced by mechanisms opposite to those quoted above.

Hiccoughs, which occur frequently during anaesthesia, produce a sharp fall in intrathoracic and hence oesophaged pressure, of a degree greater than that seen in normal spontaneous respiration.

During artificial ventilation, the intrathoracic pressure will rise with each imposed breath. The fluctuation in intrathoracic pressure will increase the pressure within the oesophagus. These fluctuations will increase in size if there is a reduction in chest wall compliance, as for example if the degree of muscle relaxation is becoming inadequate due to metabolism or breakdown of administered relaxant drugs. An increase in fluctuation can be seen with changes in ventilator function, either deliberately imposed or occurring accidentally, and also with an improvement in lung compliance, or a reduction in airway resistance allowing the imposed pressure waveform to be transmitted to the intrathoracic compartment more completely. Such an increase in lung compliance will occur if gas or liquids are removed from the pleural space or if collapsed alveoli are re-expanded.

The fluctuations may be reduced by similar mechanisms acting in the opposite direction.

Any fluctuations in intrathoracic pressure will affect not only the pressure in the oesophagus but also the vessels within the chest. The pressure in the veins (CVP), the heart, the pulmonary artery (PAP) and the pulmonary blood drainage (left atrial pressure LAP, pulmonary capillary wedge pressure PCWP) are commonly used, usually with measurements of flow (cardiac output CO) to derive parameters related to cardiac function and vascular resistance. Since all the pressures are affected by the intrathoracic pressure, it is of advantage to the physician to display these parameters not only as the raw data but also in relation to intrathoracic pressure.

The oesophageal pressure reflects the intrathoracic pressure when the muscle of the oesophagus is not contracting. It is therefore to the advantage of the physician to subtract the pressure generated in the oesophagus or some weighted factor derived from that pressure from simultaneously measured cardiovascular pressures or respiratory pressures in order to derive transpulmonary and transvascular pressures.

In a further aspect of the invention, there is therefore provided apparatus for monitoring patients comprising means for deriving a signal indicative of pressure in the oesophagus, and comparator means for deriving from the said signal separate signals indicative respectively of degree of anesthesia, cardiac activity and respiratory activity. A method of monitoring patients utilising such apparatus is also provided.

The signals indicative of pressure within the oesophagus may be displayed and also fed via a filter into a comparator to isolate low level pressure fluctuations, for example 0.2 mm Hg and/or with a frequency of more than 30/minute may be isolated from them for example by means of a filter, a comparator, or utilising a phase-locked loop circuit. These fluctuations are due to cardiac activity. The signal derived from such fluctuations may be subsequently processed to derive and display heart rate and an output related to the size of or rater of rise of the signal displayed in relation to a control level selected by the physical to indicate an increase or decrease in cardiac activity or rate.

Warning, or alarm signals can be generated by any increase or decrease in cardiac activity detected by this system, with alarm limits set for example at a 10% change, and a reset switch may be provided to allow the physician after reviewing the patient condition to reset the warning or alarm signals to the current level.

Similarly at a greater level of pressure change, the provision of a suitable filter for pressure fluctuations of for example 2–20 mm Hg and at a frequency of for example less than 60 per minute, may be used to generate signals. In addition a display of the range of pressure change with spontaneous or imposed ventilation may be provided and by the use of suitable threshold settings related to a level of fluctuation preset by the physician. Warning or alarm settings may be provided at for example a change of 10% of the preset level to indicate a change of patient condition, ventilator or circuit behaviour. In addition, by the rate of fall of and the degree of fall of intrathoracic pressure outside present alarm settings, a warning or alarm setting may be generated to indicate the incidence of hiccoughing.

By multiplexing the derived signal with other physiological signals, further information may be derived and displayed. For example by analysis of signals derived from the oesophagus and signals derived from sensors in the airway, the compliance of the lungs and/or chest wall and the resistance of the airways to gasflow may be measured and displayed and by the use of suitable thresholds to display, warn or alarm of changes of for example 10% of control levels.

Similarly, by the analysis of signals derived from the oesophagus and signals derived from sensors in the cardiovascular system, transvenous pressure may be displayed to indicate the filling pressure of the heart and to differentiate for the physician between venous pressure changes generated by changes in ventilatory or lung function and those generated by a change in cardiovascular function or the degree of distension of the intrathoracic capacitance vessels. The measured cardiovascular pressures may be corrected by subtraction of the intro-oesophageal pressure, or the change in that pressure, or the correction may be weighted according to data derived from airway monitors and according to the parameter considered.

The same sensor in the oesophagus may be used to provide a signal indicative of oesophageal contractions. The sensor may be arranged to produce, for example a signal proportional to pressure changes in the oesophagus generated by the contraction. Suitable means, for example, a filter or comparator may be provided to isolate the part of the signal due to oesophageal contraction, and this may be simply measured, or preferably also displayed.

Oesophageal activity may be derived from the said signals either from a direct display of the pressure changes or analysis of a signal derived from the peak pressure, from an integral of the waveform, the integral of the waveform above a threshold, from the frequency with which a waveform exceeds a threshold or from analysis of the rate of rise of pressure above a preset threshold. A display may be provided of the activity of the oesophageal muscles indicative of the depth of anaesthesia.

Preferably the output is derived from the rate of generation of signals in excess of a preset threshold produced by oesophageal contraction.

Accordingly, patient monitoring apparatus according to the invention may comprise a sensor for producing signals indicative of oesophageal pressure, and means of producing an output indicative of the rate and/or degree of cardiac acitivity, the rate and/or magnitude of pressure changes produced by both spontaneous ventilation and imposed ventilation, the incidence of hiccough, the level of and change of absolute pressure and the degree of oesophageal muscle activity.

Such apparatus may be provided with means for discriminating between the various signal levels, and rejecting signals outside the relevant range for each parameter. The pressure fluctuations generated by oesophageal contraction usually exceed 30 mm Hg, that of ventilation is typically less than 20 mm Hg, whilst those generated by cardiac function are typically up to 2 mm Hg. Each waveform also has a typical frequency, that due to the heart occuring 50–180 per minute, that due to respiration 5–50 per minute, that due to oesophageal activity less than 5 per minute. Signals may thus be analysed for frequency and for amplitude for example by the use of a suitable filter or comparator.

Furthermore, in order to minimise spurious signals arising from irregularities in the pressure waveforms, an inhibition period may be provided for other, lower amplitude signals immediately following each detection of the two higher amplitude signals i.e. a signal in excess of the threshold. A convenient value for the inhibition period is 5–10 seconds for oesophageal contraction, one second for respiratory fluctuation and 0.3 seconds for cardiac activity, and convenient threshold values are 25 mm Hg for oesophageal contraction, 5 mm Hg for respiratory activity and 1 mm Hg for cardiac activity.

As indicated in European patent application No. 0050983, the level of anaesthesia of an anaesthetised patient may be monitored by measuring contractions in the lower oesophagus, in the region where the surrounding muscle is smooth, i.e. involuntary. By providing a second sensing means on a probe for measuring oesophageal pressure, adapted to lie in use in the upper oesophagus, it is possible to form simultaneously an assessment of the degree of muscle relaxation of the patient. Muscle in the upper oesophagus, at the level of the cricopharyngeus, is of the striated variety, and thus susceptible to the action of muscle relaxants.

The measurement in the upper oesophagus is preferably carried out between 15 and 20 cm from the incisor teeth.

Contractions in the upper oesophagus may occur spontaneously, or may be provoked. They may be displayed directly, or preferably via a comparator, expressed and displayed either as the peak height of the contraction above a preset threshold, conveniently 10 mm Hg, or preferably as a percentage of some previous peak pressure selected by the operator. Alternatively and preferably, the contractions may be displayed as a percentage of the peak height of simultaneously occurring spontaneous or provoked lower oesophageal contractions. The display may conveniently be in the form of a trend with time, allowing the operator to observe the increasing peak height with time as the relaxants are metabolised or excreted.

The signals obtained from the monitoring equipment may be displayed as the raw data on a visual display unit or as hard copy, and may be multiplexed with other physiological signals. The derived data may be similarly displayed. For example a transducer may be inserted into the respiratory tract, and the difference between the oesophageal pressure and the pressure in the oesophageal tract measured in combination with a flow signal from a transducer in the respiratory tract. This can generate signals related to airways resistance, and lung and chest wall compliance, giving indications of changes in lung mechanics.

In general, apparatus according to the invention may comprises an oesophageal probe containing one or a plurality of balloons and/or lumens, for example of the type described in European Patent Specification No. 0050983, and a control unit containing the necessary control and/or timing and measuring apparatus to apply fluids under pressure to the appropriate lumens with the desired timing, and for measuring pressure in others of the lumens. Thus, in general it is necessary to connect one or more lumens under pressure to corresponding passageways within the control unit. It is highly desirable that means should be provided for ensuring that, before any pressure is applied to the corresponding passageways in the control unit, the corresponding probe is in fact connected, and is connected correctly. We have discovered that it is useful to provide a connecting device between the various fluid passages including a magnetic insert, and a corresponding sensing device, to enable determination to be made by the control unit of when the probe is connected.

According to yet a further embodiment of the invention therefore, there is provided a connecting device for a fluid, comprising a first connector member including at least a first fluid passage, and a second connector member including at least a second fluid passage, the first and second connector members being adapted to be releasably secured together so as to bring the said first and second fluid passages into communication with each other, a magnet associated with the first connector member, and a magnetic sensor associated with the second connector member adapted to sense the presence or absence of the said magnet, and means associated with the magnetic sensor for preventing the application of a fluid to the second fluid passage in the presence of the said magnet.

The first fluid passage will in general be the communication with the pressure sensing lumen of the oesophageal probe, and the second fluid passage in communication with some means for applying pressure, within the control unit. The first and second connector members preferably include third and fourth fluid passages respectively, adapted to be brought into communication with each other on securing of the first and second connector members. The through passageway constituted by the third and fourth fluid passages may, for example, be connected at one end to a sensing balloon and at the other end to means incorporating a pressure transducer.

In a particularly preferred embodiment, the control unit may comprise means for applying intermittent pressure waves to an oesophageal probe, and for sensing the response caused thereto, for indicating whether or not the connections between the respective first and second, and third and fourth passageways in the connector are sound. Accordingly, in a further aspect of the invention, there is provided an oesophageal monitoring device for monitoring and applying pressure to the oesophagus of a patient, comprising, means for applying intermittent pressure waves to an oesophageal probe, a connector for connecting an oesophageal probe to the aforesaid means, means for enabling the measurement of pressure in a lumen of the oesophageal probe, and control means for applying a controlled pressure to the said probe via the connector, for sensing the response caused thereto in the measurement enabling means, and for indicating lack of integrity of the probe or connection.

The means for applying pressure may comprise a syringe pump as disclosed in Europen patent application No. 0050983, or as disclosed hereinafter, but may alternatively comprise a pump, with or without a reservoir, a diaphragm vibrator, or an ultrasonic transducer.

The control means may be adapted to operate automatically, for example when connection is effected between the two parts of a connector.

We have also discussed that monitoring of pressure in the oesophagus can be usefully employed not only in anaesthetised patients but also in patients receiving sedation or analgesia, and that the monitored function relates to the degree of stress and the nature of and extent of suppression by drugs of the physiological response to stress. In particular, decreasing oesophageal activity is seen when the response to stress is inhibited or reduced by drugs.

A number of particularly preferred embodiments of the various aspects of the invention will now be described with reference to the accompanying drawings, in which:

FIGS. 1a to 1d and 2a to 2c, and 3, illustrate various oesophageal probes,

FIG. 4 illustrates circuitry associated with a microphone and loudspeaker.

FIG. 5 is a cross section of a preferred oesophageal probe,

FIGS. 6a to 6b illustrate connection devices, and

Figure 1A:
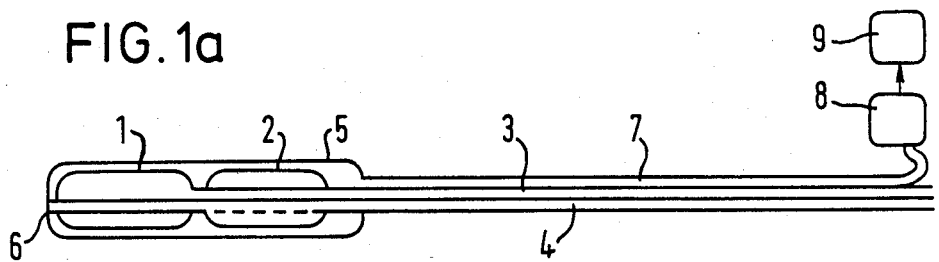

Referring first to FIG. 1a, a probe for sensing contractions in the oesophagus comprises a sensing balloon 1, and a provoking balloon 2, of the kind disclosed in European Patent Specification No. 0050983. Balloon 1 is connected by lumen 3 to a sensing transducer (not shown) and provoking balloon 2 is connected by lumen 4 to a control unit which includes means for generating pressure. An outer protective envelope 5 surrounds both balloons 1 and 2, and is sealed to the distal part of lumen 4 at the tip 6 of the probe. A third lumen 7 is connected to the inner space of the envelope 5, to enable any leakage from the provoking balloon 2 to be vented.

Such leakage may be detected by a transducer 8, conveniently a heated thermistor, and used to trigger an alarm circuit 9. The transducer 8 and alarm 9 may preferably be included in the control unit.

Figure 1B:
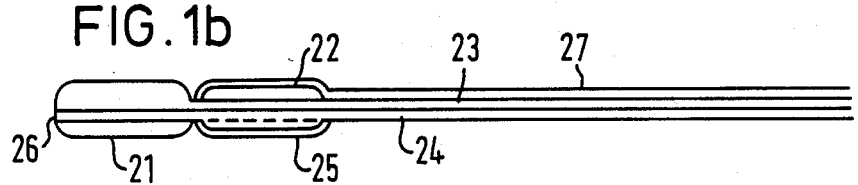

The probe of FIG. 1b is generally similar to that of FIG. 1a, parts 21 to 27 corresponding to parts 1 to 7 of FIG. 1a. The envelope or sheath 25 is sealed between the sensing balloon 21 and the provoking balloon 22.

Figure 1C:
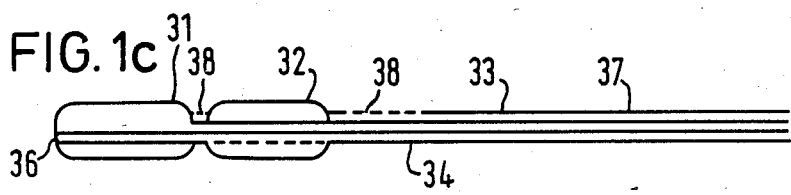

A preferred alternative embodiment is illustrated in FIG. 1c, in which parts 31 to 36 correspond with parts 1 to 6 of FIG. 1a. In this case however, a third lumen 37 is connected not to an envelope surrounding sensing balloon 31 and provoking balloon 32, but instead vents directly into the oesophagus by means of holes 38. Any leakage into the oesophagus will therefore pass through holes 38 and into lumen 37. The leakage can then be detected by a sensor in the same way as in FIG. 1a.

Figure 1D:
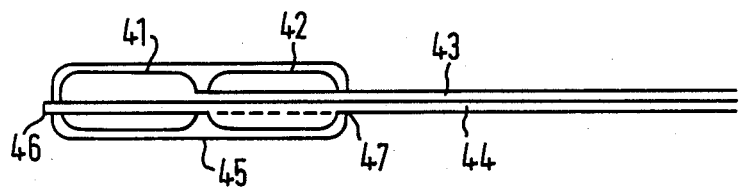

A further alternative embodiment is illustrated in FIG. 1d. In this embodiment, an envelope 45 is sealed at both its distal and proximal ends 46 and 47. The envelope thus surrounds completely a sensing balloon 21, and a provoking balloon 42, connected via lumens 43 and 44 respectively. Leakage from provoking balloon 42 will cause the pressure in sheath 45 to rise, and thus cause pressure to be applied to the sensing balloon 41. This rise in pressure can be sensed by the transducer (not shown) used to detect the oesphageal contractions by measuring pressure in balloon 41. An alarm circuit may be triggered if the pressure exceeds a predetermined level and time span, for example 50 mm Hg, and 10 seconds duration. A microphone or other means for monitoring heart and breath sounds may be incorporated in any of the various balloons (e.g. 1, 21, 31, 41) or lumens (e.g. 3, 4, 23, 24, 33, 34, 43, 44), and they give additional warning of leakage.

Figure 2A:
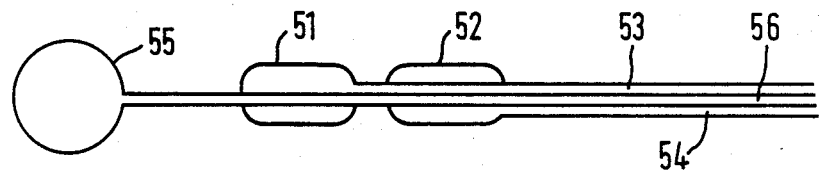
Figure 2B:
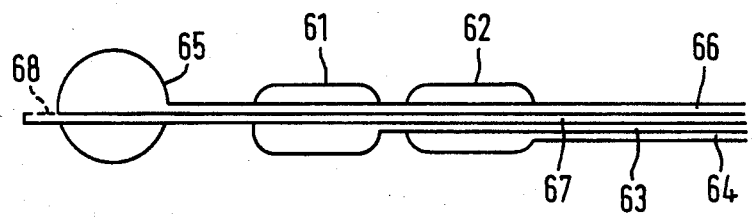
Figure 2C:
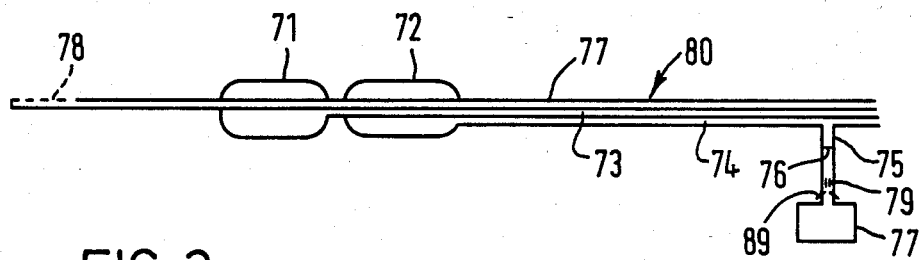

FIGS. 2a to 2c illustrate yet further alternative probes, suitable for use with the method and apparatus disclosed in European patent application No. 0050983. The probes of FIGS. 2a and 2b, in addition to sensing balloons 51 and 61, and provoking balloons 52 and 62, connected via lumens 53, 63, 54, and 64 respectively, include at their distal end further balloons 55, 65, adapted to lie inside the stomach. This balloon is initially deflated whilst the probe is inserted through the oesophagus, and is inflated once the balloon (55, 65) is inside the stomach. The balloons 55, 65 may conveniently have a volume from 20 to 50 cc. When the balloons 55, 65 have been inflated, the probe may be gently withdrawn until it impacts the oesophago-gastric junction. This enables the sensing and provoking balloons 51, 61, 52, 62 to be located at the correct position in the lower oesophagus. The gastric balloons 55, 65 may conveniently be located at a distance from 5 to 10 cm from the respective sensing balloons 51, 61. In the probe of FIGS. 2b and 2c, a further lumen 67, 77 is provided, which extends a minimum of 20 cm distally of the respective sensing balloons 61, 71. The lumens 67, 77 have a plurality of orifices 68, 78 respectively, to enable gastric aspiration to be performed.

Any of the above probe designs may incorporate an additional balloon to allow an earpiece to be attached, to permit the physician to monitor the heart, and breath sounds of the patient by means of an earpiece or microphone.

Figure 3:
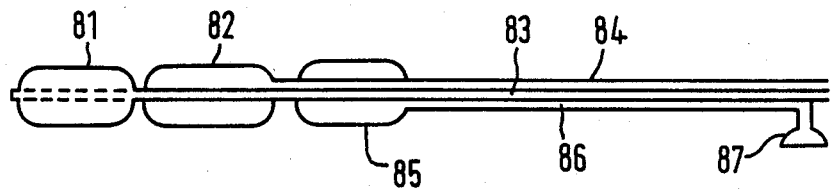

Such an embodiment is illustrated in FIG. 3. In the embodiment of FIG. 3, a sensing balloon 81, is connected via a lumen 83, and a provoking balloon 82, is connected via a lumen 84 to the usual transducer and provoking arrangements. A third balloon 85 is connected via lumen 86 to an earpiece or microphone 87. An alternative arrangement is illustrated in FIG. 2c. The lumen 74 attached to the provoking balloon 72 of the embodiment of FIG. 2c includes a side passageway 75 leading to an earpiece 77. Interposed between the side tube 75 and the earpiece 77 is a flexible diaphragm 76, which prevents the pressure applied to the provoking balloon 72 via the provoking apparatus reaching the earpiece 77, whilst allowing sounds transmitted through the fluid in the passageway 74 to reach the earpiece. Also interposed between the tube 75 and earpiece 77 is a flow restrictor 79, in the form of a plurality of capillary tubes, to protect the physician in the event of failure of diaphragm 76. The earpiece 77 is connected to the side tube 75 by means of a releasable connector 89.

Alternatively and preferably, a microphone may be incorporated into the lumen associated with the sensing balloon, or, more preferably, that associated with the provoking balloon. Preferably, means are provided for inhibiting noise associated with provocation of the oesophagus, and a suitable system is illustrated in FIG. 4.

In the device of FIG. 4, a transducer 90, for example, a microphone, is connected to, for example inserted in, a lumen 91. The transducer 90 is preferably separated from the interior space of the lumen 91 by a diaphragm 92. The signal from the transducer 90 is amplified by an amplifier 93, and the output used to drive a speaker 94. Alternatively, an earpiece 95 may be used, utilising a switching jack socket 96 which disconnects the speaker 94 when the earpiece 95 is in use.

A comparator 97 detects the occurence of a provocation cycle, and during the provocation cycle inhibits the output from the amplifier 93.

An acoustic signal can be generated from the pressure waveform sensed by the sensing transducer, and the output of the sensing transducer fed directly to the amplifier 93.

The sensing and provoking balloons in the various probes may preferably each have a volume of from 2 to 10 c.c., a length of from 3 to 10 cm, and a maximum diameter of approximately 2 cm.

The probes described above are all preferably fluid filled, the sensing balloon being liquid filled, and the provoking balloon gas filled. However, any or all of the various balloons may be self inflating, and may for example have an internal filling. Such probes may be inserted into the oesophagus by prior deflation.

As an alternative to the above-described probes including a sealed pressure sensing balloon, pressure in the oesophagus may be sensed by measuring the back pressure generated in a simple open ended probe, through which a saline solution is passed. The open end of the probe may be positioned about 35 cm from the incisor teeth, and the flow rate of saline solution utilised may be very slow, for example 10 ml/hr.

In addition to providing within the probes passages for permitting egress of fluid, for example as in the probe of FIG. 1c above, the cross section of the stem of the probe may be such as to define a passage between the material of the probe and the wall of the oesophagus. FIG. 5 illustrates a possible formation of such a cross section, which could for example be used with the probe of FIG. 2c. The probe stem 80 comprises lumens 73, 74 and 77 as shown in FIG. 2c. The external shape of the stem 80 is such as to define a space 105, which will form a fluid passage when the probe is in use in the oesophagus. The cross section illustrated in FIG. 5 may be utilised as an additional safety measure with any of the probes used in accordance with the invention.

A material which is opaque to X-rays may be incorporated into, for example, the tip or the wall, of any of the aforesaid probes.

Distance markings may be applied, typically at 30 and 35 cm from the tip of the probe, so that the provoking and sensing balloons may be accurately positioned in relation to the incisor teeth.

Any or all of the probes may be modified to include means, for example thermistors, to measure body temperature. In addition, electrodes may be incorporated to record the electrocardiogram, either within the oesophagus, or between the oesophagus and some part of the chest wall. Furthermore, impedance measurements of body tissues may be measured, either within the oesophagus, or between the oesophagus and some part of the chest wall. This latter method allows the impedance pathway to be selected to include largely cardiovascular structures or largely pulmonary structures.

Any of the aforementioned probes may include fibre optic channels, to enable the assessment of the oxygenation of the mucosa of the patient. This provides a useful measure of the general level of oxygenation of the patient. To this end, separate optical fibre materials may be incorporated into the probe wall. Alternatively and preferably however, the material of the flexible probe itself may be utilized as an optical fibre, and optical equipment may be attached to the proximal end of the probe, to enable the colour of light passing through the probe wall to be assessed. Although the material from which the probe is constructed may not be an ideal optical material, such measurements of colour need be only fairly approximate, and thus measurements made using the probe wall as an optical channel may suffice. A light source may be provided at the proximal end of the probe for illuminating the interior of the oesophagus, and the probe wall may preferably be also be used as a light channel to conduct light from the light source into the oesophagus.

As indicated above, a typical probe length will allow from 30-35 cm to be within the oesophagus, and will be marked at this distance to facilitate correct placement. However, smaller sizes with shorter and/or smaller balloons may be constructed for paediatric and neonatal use.

The sensing balloon is preferably liquid filled, and the lumen attached to the sensing balloon may preferably include a hydrophobic filter, to allow gas to escape from the sensing balloon whilst the balloon and respective lumen is filled with water, whilst not permitting the passage of the fluid with which the balloon is filled.

There are many tubes which may be used in patients receiving anaesthetics, sedation or analgesia. It is important that any connections by means of which the various probes are connected to apparatus for generating pressure in them or monitoring pressure, should not permit connection to any other apparatus which might be used in connection with patient care, for example intravenous infusions or the like. It is therefore desirable to provide a connecting device which is asymmetric, and which cannot be connected to other existing devices. Such a device is illustrated in FIGS. 6a to 6b.

FIG. 6a is an end view of the centre part of a connector 125. Tapered sockets, 106, 107, and 108 are connected to respective fluid passageways 109, 110, and 111. FIG. 6b and 6c show longitudinal sections through respectively the connector part 125 adapted to be connected to the end of a flexible probe, and a second connector part 124, adapted to be panelmounted and to connect thereto. A free threaded collar 118 is adapted to engage a fixed threaded collar 113 mounted on panel 120. Conical projections 121, 122, and 123 project from the base of the socket part 124, and are shaped so as to engage with conical sockets 106, 107, and 108 respectively. Each projection 121, 122, and 123 has a through passageway 115, 116 and 117 respectively. In use, first connector member 125 is releasably secured to second connector 124 by means of threaded collar 118.

Thus, fluid passageway 119 on first connector part 125 is brought into communication with fluid passageway 115 on second connector part 124. Similarly, third fluid passageway 110 on part 125 communicates with fourth passageway 116, and fifth passageway 123 with sixth passageway 117. Sockets 106, 107 and 108 taper to different extents, socket 106 tapering from 6 mm to 4 mm diameter over a length of 6 mm, socket 107 from 4 mm to 2 mm over the same length, and socket 108 from 5 mm to 3 mm over the same length. A groove 112 in the first connector part assists accurate mating and locates with a lug 14 on the second connector 125.

A magnetic insert 128 is incorporated into connector part 125, and causes the operation of a reed relay 129 when the two connector parts are secured together. A Hall effect transducer may be used as an alternative to a reed switch.

Although FIGS. 6a to 6b show a connecting device incorporating, in all, six fluid passages adapted for connection in three pairs, it may be desirable to provide only one or two fluid passage connections, with certain of the probes described above and in European Patent Specification No. 0050983. In particular, the lumen of the probe attached to the sensing balloon may not be passed through a connection device, but may be terminated externally of the main control equipment with a simple transducer. Thus, the connector may be used only for the lumen connected to the provoking balloon, and, if used, the lumen for detecting leaks.

Magnetic insert 128 may be provided within one of the conical sockets 107, 108, in the event that such socket is not required for fluid connection purposes.

As indicated in European Patent Specification No. 0050983, circuitry and hardware associated with provoking the oesophagus and sensing the response may conveniently be housed in a single console unit, and the connector part 124 may conveniently be mounted on a panel of such a console unit. The console unit also comprises means, for example an electrically operated valve (not shown) for preventing the application of a fluid to the fluid passages 115, 116 and 117 until the reed switch 129 has been actuated by the magnetic insert 128.

Furthermore, the console unit may include an automatic self test mechanism, in accordance with which actuation of the reed switch 129 caused by connection of the two parts 125 and 124 of the connector causes a pressure to be applied to passageway 115, according to a preset test sequence, for example a plurality of regular bursts may be applied. The corresponding pressure rise applied to through passageway 116 is then sensed by a transducer within the console unit, to ascertain whether it shows corresponding fluctuations, within preset limits. This is particularly useful with a probe of the kind shown in FIG. 1a, in which the pressure in envelope 5 may be sensed, as pressure is applied to the provoking balloon 2.

Alternatively, connections may be effected within the console unit to connect the sensing transducers to the means for applying pressure to the provking balloon. In this way, the response of the sensing transducers can be checked, and if necessary the gain of any amplification circuit associated with them may be adjusted, automatically or manually. The magnitude of the signals obtained may be stored, and used in subsequent analysis to detect leakage or overinflation.

Furthermore, the automatic test sequence may measure the pressure produced in the provoking balloon by a given pressure impulse and may measure the pressure decay over a period of time, to indicate leakage from the provoking balloon.

In all the probe devices discussed above, it is desirable to be able to provide a metered amount of fluid, normally air, to the provoking balloon to stimulate the oesophagus. In a preferred embodiment, this may be achieved by including within the pressure line between the source of pressure and the pressure lumen (eg. lumen 4 in FIG. 1a) an isolating chamber, of the kind shown in FIG. 7.

Figure 7:
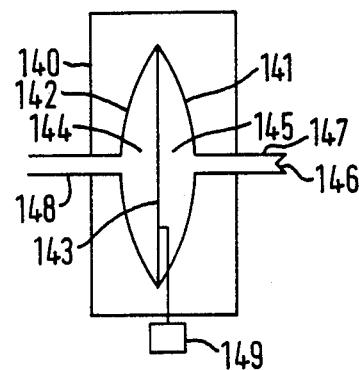
FIGS. 7 and 8 illustrate pressurising mechanisms for a provoking balloon.

The chamber of FIG. 7 has an outer container 140 containing two spherically dished plates 141 and 142 having a diaphragm 143 sealed to each plate at the edges of the plates, so as to define two compartments 144 and 145. A source of intermittent pressure 146 is applied to an inlet pipe 147, and distends the diaphragm 143 to cause the metered volume of air contained within compartments 144 and 145 to be displaced into outlet pipe 148. A movement transducer 149 is connected to diaphragm 143. Control equipment (not shown) is provided to generate an alarm if the displacement of the diaphragm 143 exceeds predetermined limits on any cycle of operation, or if transducer 149 is not actuated at least once for each provoking pressure pulse applied by means 146.

Figure 8:
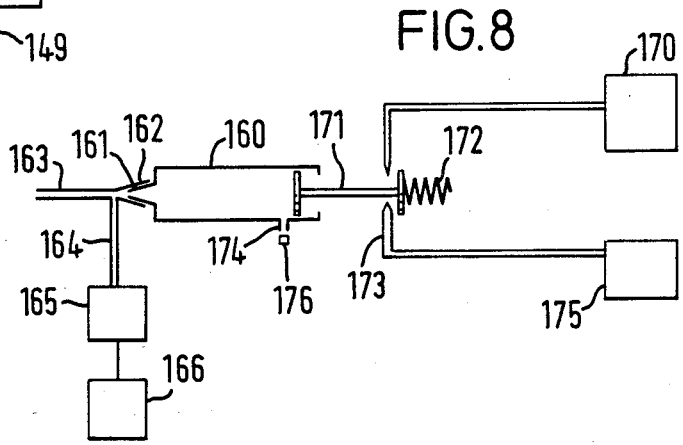

Other shapes of reservoir may be used as an alternative to that shown. Alternative means of applying pressure to an oesophageal balloon probe is shown in FIG. 8. The pressure applying device in FIG. 8 include a syringe 160, typically having a volume of 10 ml. The syringe 160 has a tapered nozzle 161, which may preferably be so tapered as to fit the appropriate socket 106 of connecting device of FIG. 6a, to enable the syringe to be used directly with the connecting device if desired. Generally however, the tapered nozzle 161 mates with a corresponding tapered socket 162, within the console unit.

A conduit 163 leads from the base of the tapered socket 162 to a connection unit of the kind shown in FIG. 6c. A second conduit 164 leads from the base of the socket to a pressure transducer 164. A stepper motor 170 is arranged to withdraw the plunger 171 of the syringe, against the action of spring 172, until a latch 173 is engaged. At this point, the position of plunger 171 is such as to vent the inner space of the syringe to the ambient atmosphere by means of side vent 174 in the syringe body. When it is desired to cause pressure to be applied to lumen 163 to cause oesophageal provocation, a solenoid 175 releases latch 173, causing the piston 171 to be driven forward under the action of spring 172. As it is driven forward, piston 171 occludes orifice 174, and thus delivers a metered volume of air to lumen 63. The pressure generated may be monitored by transducer 165, utilising comparator 166, and the value detected used for sensing leakage and the like, as described above. In particular, the comparator 166 should sense a pressure plateau when the plunger 171 reaches the end of its travel. If the balloon to which the pressure is applied is over-distensible, or punctured, the pressure plateau will be lower than expected. Similarly, if th value of the plateau falls by more than, say, 10% of the original value over a preset period, an alarm may be generated.

Anaesthetic gases diffuse freely into and out of body cavities, and thus it is likely that gases will diffuse into a gas-filled provoking balloon of the probes according to this invention. It is therefore desirable to provide means for equalising the volume within the pressure generating means, and this is achieved by means of orifice 174. A transducer 176 is provided adjacent the orifice 174 to detect any large and unexpected flow of gas into or out of the syringe.

Diagram 9 shows a particularly preferred embodiment of the pneumatic circuit which may be employed for provocation of the oesophagus and for the monitoring of heart sounds. Reservoir 901, conveniently of 400 cm$^3$ capacity, pressurised by pump 902. The pressure in the reservoir is conveniently 200 mm Hg and is limited by a pressure switch 903 which inhibits pump 902 when the pressure reaches the preset limit. Between provoking cycles a provoking balloon (not shown) in connected via lumen 905 and valve 904 to lumen 912 and via valve 910 to a vent 911 to atmosphere. The valve 906 connects lumen 905 with a stethoscope or microphone 907. At the start of the provocation cycle valve 906 closes lumen 907 to protect the physician. The valve 910 closes, and valve 904 connects the reservoir 901 via lumen 913 to the provoking lumen 905. After a period of time, conveniently 0.5 sec, valve 904 connects lumen 905 to reservoir 908, conveniently 25 cm$^3$ capacity. The pressure in the sealed compartment comprising provoking balloon, lumen 905, lumen 912, reservoir 908 is monitored by transducer 909. By the use of suitable circuitry (not shown) a low pressure or a fall in pressure which would indicate leakage or disconnection is detected, and may generate alarm signals and inhibit the provoking cycle. After an interval, conveniently 5 secs, the provoking cycle ends and valve 910 opens to vent the system to atmosphere via vent 911. Valve 906 subsequently reconnects the stethoscope or mircophone 907 to lumen 905 enabling heart sounds and breath sounds to be monitored between the provoking cycles. Valve 906 remains closed whenever valve 910 is closed or valve 904 connects lumen 913 to lumen 905, thus minimising the risk of pressurising stethoscope or microphone 907. Pump 902 is inhibited if valve 906 is closed, valve 910 is closed, or valve 904 connects lumen 913 to lumen 905, thus minimising the risks of over-pressurising the provoking balloon.

Figure 10A:
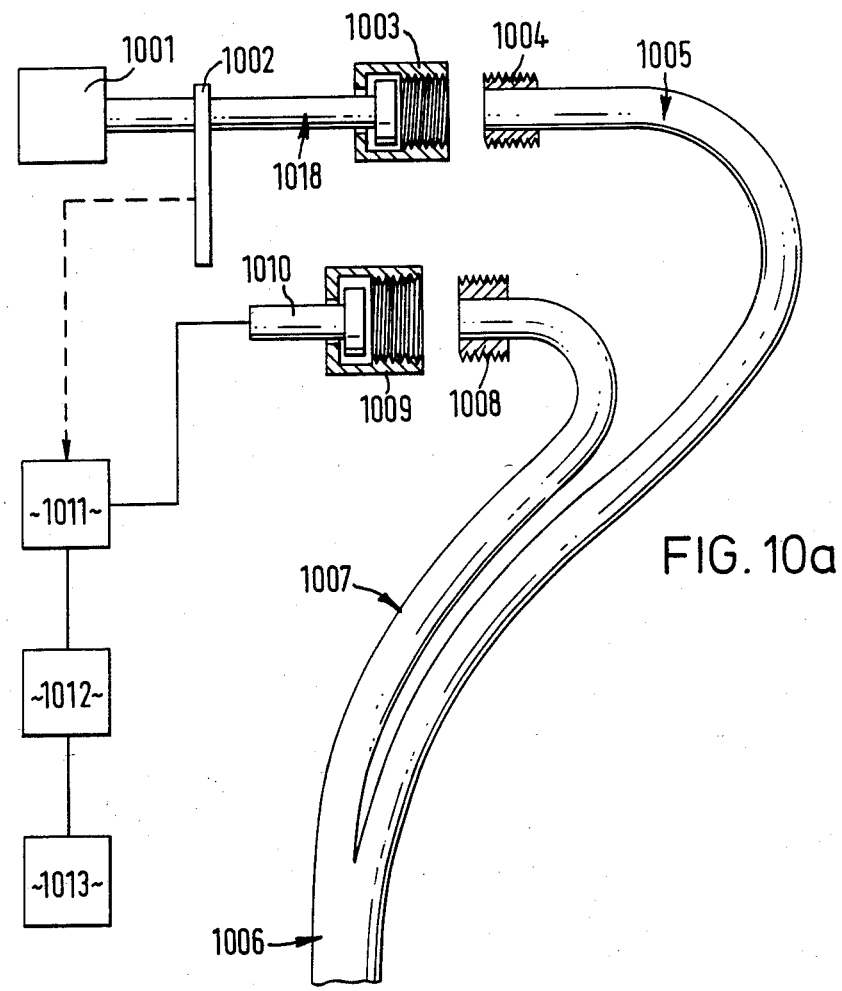
FIGS. 10a and 10b illustrate fibre-optic measurement apparatus.

FIG. 10a illustrates a fibroptic saturation meter to be incorporated with the oesophageal monitoring system. A light source, 1001, passes white light through a rotating filter disc 1002 with alternative filters trasmitting light at wavelengths 650 and 800 nanometers respectively. The source is coupled via a light-proof threaded collar 1003 and mating coupling 1004 with a fibre bundle 1005 transmitting light via a single bundle 1006 to a convenient point in the oesophagus. Reflected light is gathered by the fibroptic bundle 1007, and the collected light passes through a light proof connection incorporating a threaded collar 1009 and a mating collar 1008 to a photomultiplier 1010. By means of a gated circuit 1011 and a ratio circuit 1012 the ratio of red light reflected to that of infra-red light is calculated and displayed or recorded on unit 1013. This ratio is know to be proportional to the saturation of blood, and can be displayed as haemoglobin saturation. Mucosa is richly supplied with blood vessels and consumes little oxygen in the oesophagus, and therefore this figure is closely related to arterial blood oxygen levels. Suitable alarm levels may be preset to trigger an alarm circuit if the oxygen level in blood falls below a preset level.

The light source and filters may be replaced by suitaable light emitting diodes, and the photomultiplier by photodetectors.

Figure 10B:
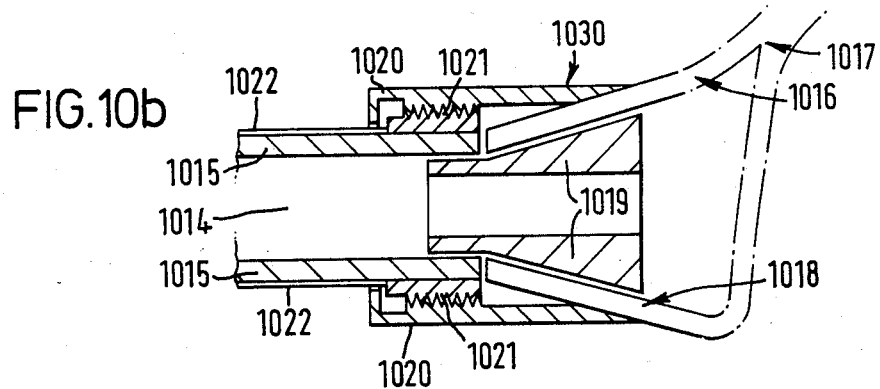
Figure 13A:
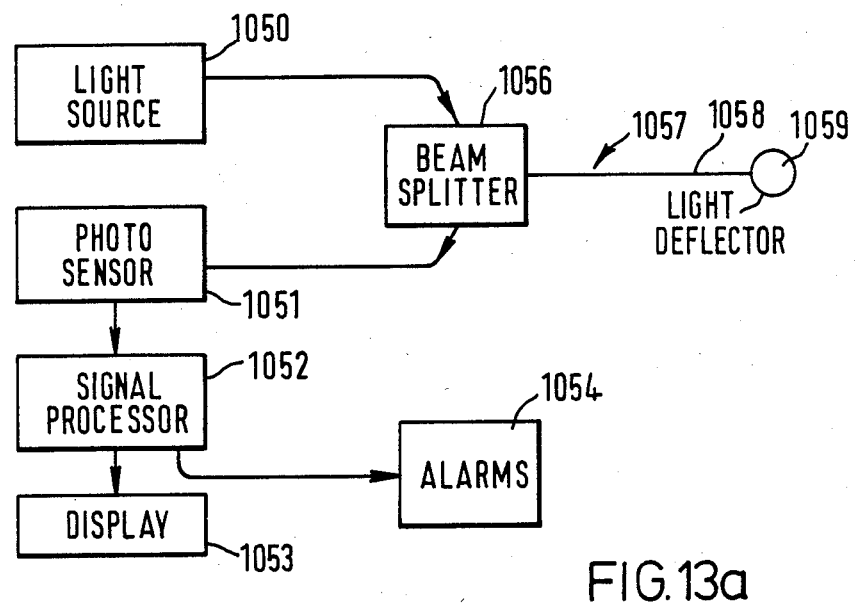
Figure 13B:
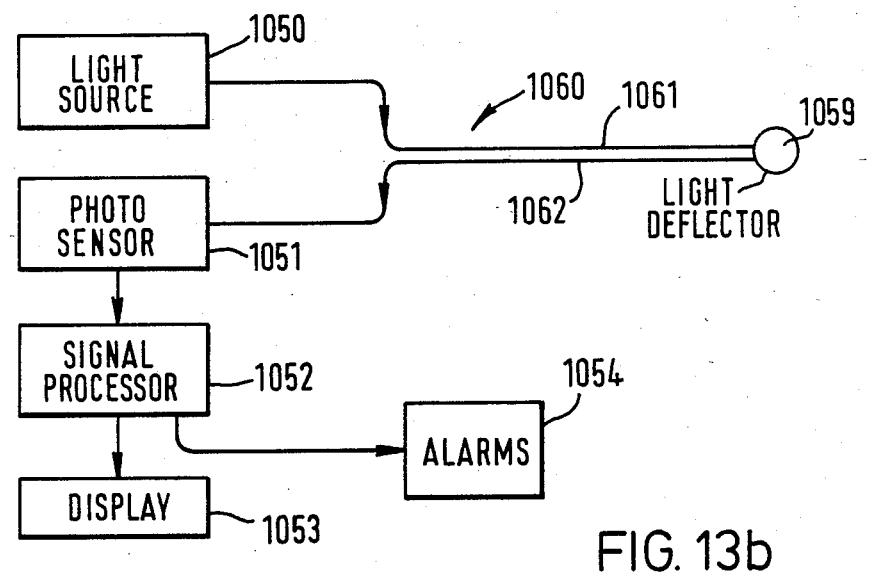

In addition one or both of the fibre-optic channels may be replaced as shown in FIG. 10b, by using the wall of the oesophageal probe.

In FIG. 10b, a fibre-optic light guide 1017 is divided into two parts 1016 and 1018. These two parts 1016 and 1018 are conducted to a connector 1030 and 1019 for the various fluid passageways to the probe (only 1, 1014, shown for clarity). In the connector, the two parts 1016 for 1018 surround the fluid passageway 1014 circumferentially, and conduct light to the walls 1015 of an oesophageal probe.

The parts 1016 and 1018 mate with the wall of the probe 1015 by way of the mating light proof collars 1020 and 1021. An optional reflectant surface 1022 may be applied over the upper part of the probe to prevent loss of light from the outer surface, the reflectant surface being omitted over for example, 15 cms of the distal end of the probe. The probe wall may thus replace part of, or both, elements of the fibre-optic pathway 1006 of the probe shown in FIG. 10a. If both channels of the fibroptic pathway are to be replaced, a proportion of the circumference of collar 1016 may be connected to the transmitting part, and a proportion to the receiving part of the light circuit. The two parts 1016 and 1018 of the light guide may be divided by a light proof divider within the connector 1030 such that the transmitting circuit is isolated from the receiving circuit.

Muscle relaxants are frequently used in anaesthesia and intensive care. They affect mainly striated, voluntary muscle and will reduce the ability of that muscle to contract, whilst having little or no effect upon smooth, non-striated muscle. The upper end of the oesophageal musculature consists of striated muscle and the lower end, of smooth muscle. When muscle relaxants are given, the ability to contract of the upper end of the oesophagus will diminish and hence the peak height of contractions will fall, as will the length of time a contraction produces a pressure above a preset limit, the area under the curve of that contraction and the rate of rise of pressure during that contraction. The ratio of the parameters to the corresponding parameters of provoked or spontaneous lower oesophageal contractions will also fall. Recovery will slowly occur as the drug is metabolised or more quickly as reversal agents are given. By monitoring the signals, conveniently pressure, from the upper end of the oesophagus, and also by comparing them with those from the lower end of the oesophagus, the state of muscle relaxation, the requirement to give reversal agents or to add further relaxants can be assessed. It may also be convenient to compare the contractions produced in the patient with the same signals produced before relaxants were introduced to give a normal, control, measurement with which to compare the current value.

According to yet a further aspect of the invention, there is therefore provided a method for determining the degree of skeletal muscle relaxation of a patient, which method comprises providing signals indicative of contractions at two spaced points in the oesophagus of a patient, and comparing the signals to derive therefrom an output indicative of the degree of skeletal muscle relaxation of the patient. The invention includes within its scope apparatus for carrying out the above method.

Figure 9:
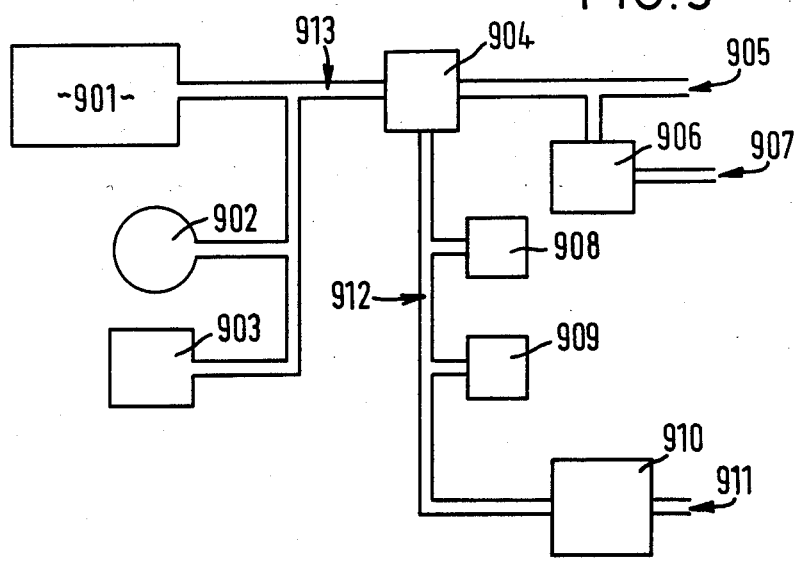
FIG. 9 illustrates a pneumatic circuit.

To measure such contractions in the upper oesophagus, means for measuring pressure, for example, a balloon or a transducer, may be provided in association with any of the probe devices disclosed above or in European Patent Specification No. 0050983. A suitable probe may be, for example, one such as that shown in FIG. 8 of European Patent Specification No. 0050983, the dimensions being such that the tip of the probe lies, in use, approximately 30 cm from the incisor teeth as indicated above, and the upper balloon, 84b about 15 cm from the incisor teeth. FIG. 9 of European Patent Specification No. 0050983 illustrates a suitable schematic control circuit for enabling the necessary information to be extracted from two such probes. The comparator shown may measure peak height, rate of rise of, or area under the curve of any contraction producing a signal from the upper oesophageal balloon above a preset limit. The output may be displayed directly or as a trend with time, or as a percentage of similar measurements produced by some previous contraction selected by the operator. Alternatively, the signal produced by the lower oesophageal sensing balloon may be used as an input into transducer A of the said FIG. 9, and the comparator adjusted to give a signal to the peak height of or area under the curve of or time above threshold or rate of rise of the signal from the upper sensor as a percentage of similar readings from the lower sensor. The signal may be displayed or recorded. Suitable alarm limits may be either preset or adjusted by the operator to give warning of too much or too little a degree of relaxation.

Optionally, the signal from the lower oesophagus may be used to derive information regarding the cardiovascular system and the respiratory system. In general, the signal derived from the pressure sensing means represents a composite of respiratory waveforms, cardiac waveforms, and waveforms due to oesophageal contractions. Pressure fluctuations above a threshold value, normally approximately 25 mm Hg, may be taken to represent oesophageal contractions, and may be dealt with as indicated above, and in European Patent Specification No. 0050983. The mean pressure between contractions represents intrathoracic pressure.

Because respiratory and cardiovascular values may be disturbed during oesophageal contraction, derivation of data relating to respiratory and cardiovascular function is preferably inhibited during oesophageal contractions, i.e. when the pressure sensed is more than 25 mm Hg. Between contractions, a comparator is arranged to sense pressure waveform with a peak-to-peak height of from 5 to 25 mm Hg. Such waveforms represent ventilation. A rate meter is connected to an adjustable threshold discriminator to allow the display of respiratory rate, and an adjustable alarm setting may be provided.

The amplitude of the respiratory waveforms may be displayed, or multiplexed with other physiological parameters or used as factors to solve equations giving lung and chest wall compliance or airway resistance. Adjustable alarms may be provided to give indicators of changing respiratory functions.

Pressure waveforms in the range 1-5 mm Hg (peak to peak) generally represent cardiac activity, and the apparatus preferably includes a discriminator to isolate signals due to pressure changes in that range, and a rate meter associated with the discriminator, to derive from the signals the cardiac rate, and display it. In the same way as described above, the detection of cardiac rate is preferably inhibited during oesophageal contractions.

Alternatively, the respiratory waveform may be derived by subtracting the oesophageal waveform after filtration, and the cardiovascular waveform similarly derived after subtraction of the respiratory waveform, and similar analysis and display performed.

The output from the comparator attached to the pressure transducer can also be used to derive and display intrathoracic pressure. The output may be multiplexed or subtracted from simultaneously measured intravascular pressures to give transvascular measurements for use in calculations of pressure and flow in the cardiovascular system, and enable the operator to discriminate between changes produced by changes in intrathoracic pressure, and those produced by changes in the status of the cardiovascular system.

It should be appreciated that the various improvements in and modifications of the method and apparatus disclosed in European Patent Specification No. 0050983 are novel and inventive in themselves, and the various aspects of the invention as disclosed herein should be understood to include such features, whether or not used with other features of the invention in conjunction with which they are particularly described. Furthermore, it would be readily apparent to those skilled in the art that numerous changes and modifications are possible, within the scope of the present invention.

We claim:

1. Patient monitoring apparatus comprising an oesophageal probe including an oesophageal balloon for provoking the oesophagus of a patient to cause contractions therein, means for applying a fluid under to the oesophageal balloon, a sensor for detecting signals indicative of oesophageal contractions in the oesophagus of the patient, means for deriving from the said signals an output indicative of the degree of anaesthesia of the patient, and means for protecting the oesophagus of the patient from leakage of the fluid from the probe.

2. Apparatus as claimed in claim 1, wherein the protection means includes an enclosure surrounding at least the provoking balloon.

3. Apparatus as claimed in claim 2, including a transducer in communication with the internal space of the enclosure, and adapted to produce a signal indicative of a characteristic of the fluid selected from flow and pressure, and wherein the apparatus includes means for preventing the application of pressure to the fluid in response to the signal produced by the said transducer to prevent the application of pressure in the event that the said signal indicates a leak in the enclosure.

4. Apparatus as claimed in claim 1, wherein the protection means includes a lumen open at an end adapted to terminate in use in the oesophagus of the patient, whereby the luman provides a venting path to the exterior of the patient for relieving oesophageal pressure.

5. Apparatus as claimed in claim 4, including a transducer in communication with the open lumen wherein the apparatus includes means for preventing the application of pressure to the fluid in response to the pressure or flow sensed by the said transducer.

6. Apparatus as claimed in claim 1 further comprising means for detecting the pressure rise in the oesophageal balloon resulting from operation of the pressure applying means.

7. Apparatus as claimed in claim 6, wherein the oesophageal probe includes a lumen for providing fluid under pressure to the oesophageal provoking balloon, and wherein the detection means is adapted to provide an indication of pressure change in the said lumen over a predetermined period of time, so as to provide an indication of leakage of fluid from the provoking balloon, or the disconnection of the provoking balloon.

8. Apparatus as claimed in claim 6, wherein the means for applying a fluid under pressure includes means for rapidly releasing pressure from a pressurised vessel into the oesophageal balloon to provide rapid inflation, and for automatically relieving pressure applied to the oesophageal balloon a predetermined period thereafter.

9. Apparatus as claimed in claim 1, wherein said protecting means includes:
 means for applying intermittent pressure waves to an oesophageal probe,
 a connector for connecting an oesophageal probe to the aforesaid means,
 means for enabling the measurement of pressure in a lumen of the oesophageal probe, and
 control means for applying a controlled pressure to the said probe via the connector for sensing the response caused thereto in the measurement enabling means, and for indicating lack of integrity of the probe or connection.

10. A device as claimed in claim 9, wherein the means for enabling the measurement of pressure comprises a pressure sensor within the monitoring device, adapted for connection to a pressure measuring lumen of the oesophageal probe.

11. Apparatus as claimed in claim 9, wherein the said control means is adapted to operate automatically on connection of an oesophageal probe to the connector.

12. An elongate probe for measuring oesophageal contractions, having a distal end adapted to pass downwardly through the oesophagus of the patient, and a proximal end adapted in use to lie externally of the mouth of the patient, the probe including a first balloon adapted in use to lie within the oesophagus of the patient, a lumen in fluid communication with the first balloon and the proximal end of the probe to enable pressurization of the first balloon for stimulating the oesophagus, to cause contractions therein, a second balloon adapted in use to lie within the oesophagus of the patient for enabling the measurement of pressure within the oesophagus, thereby to sense contractions of the oesophagus, and an enclosure around at least one of the said balloons for preventing the egress of fluid from the respective balloon to the oesophagus in the event of rupture of the respctive balloon.

13. A probe as claimed in claim 12, wherein the enclosure surrounds both the first and second balloons.

14. A probe as claimed in claim 13, including means for enabling the detection of pressure rise in the enclosure.

15. A probe as claimed in claim 14, wherein said means for enabling includes another lumen communicating with the enclosure and adapted to connect with a transducer externally of the patient for measuring pressure rise in the enclosure in said another lumen.

16. A method of monitoring the degree of anaesthesia of a patient utilizing an oesophageal of the type including an oesophageal balloon for provoking the oesophagus of a patient to cause contractions therein, means for applying a fluid under pressure to the oesophageal balloon, a sensor for detecting signals indicative of oesophageal contractions in the oesophagus of the patient, means for deriving from the said signals an output indicative of the degree of anaesthesia of the patient, and means for protecting the oesophagus of the patient from leakage of the fluid from the probe, which method comprises passing the oesophageal probe into the oesophagus of the patient, applying a fluid under pressure to the oesophageal balloon, protecting the oesophagus of the patient from leakage of the fluid from the probe utilizing the said protection means, and monitoring the degree of patient anaesthesia by deriving the same from said signals.

* * * * *